United States Patent
Gantelius et al.

(10) Patent No.: US 8,831,893 B2
(45) Date of Patent: Sep. 9, 2014

(54) METHOD FOR ESTIMATING KINETIC RATES

(75) Inventors: Jesper Gantelius, Hägersten (SE); Mats Nystrand, Uppsala (SE); Helene Andersson-Svahn, Sollentuna (SE)

(73) Assignee: Phadia AB, Uppsala (SE)

( * ) Notice: Subject to any disclaimer, the term of this patent is extended or adjusted under 35 U.S.C. 154(b) by 761 days.

(21) Appl. No.: 12/897,981

(22) Filed: Oct. 5, 2010

(65) Prior Publication Data

US 2012/0084017 A1  Apr. 5, 2012

(51) Int. Cl.
*G01N 31/00* (2006.01)
*G06F 19/00* (2011.01)
*G01N 33/557* (2006.01)

(52) U.S. Cl.
CPC ............ *G01N 33/557* (2013.01); *G06F 19/70* (2013.01)
USPC ................................ 702/30; 702/19; 702/22

(58) Field of Classification Search
CPC ...... G06F 19/70; G06F 19/701; G06F 19/702
See application file for complete search history.

(56) References Cited

U.S. PATENT DOCUMENTS

| | | |
|---|---|---|
| 2003/0073121 A1 | 4/2003 | Mendel-Hartvig et al. |
| 2007/0020768 A1 | 1/2007 | Rundstrom et al. |

OTHER PUBLICATIONS

Qian et al., Analysis of Lateral Flow Bio-detectors: Competitive Format. Analytical Biochemistry 326, 211-224, 2004.*
Gentelius, "Novel Diagnostic Microarray Assay Formats Towards Comprehensive On-site Analysis", Royal Institute of Technology, Stockholm, SE, Oct. 6, 2009.

* cited by examiner

*Primary Examiner* — Michael Borin
(74) *Attorney, Agent, or Firm* — Porter Wright Morris & Arthur LLP (57) ABSTRACT

The present invention relates to a method for estimation of kinetic characteristics for the formation and dissociation of a complex using lateral flow. The present invention facilitates an easy to use method with high accuracy.

13 Claims, 7 Drawing Sheets

METHOD FOR ESTIMATING KINETIC RATES

TECHNICAL FIELD

The present invention relates to a method for estimating kinetic on- and off-rates.

BACKGROUND

Lateral flow assay systems have been extensively used as laboratory and point of care devices over the past forty or more years for clinical diagnosis of a wide variety of physiological conditions and disease states. The popularity stems mainly from such inherent useful characteristics as short assay times, high portability, convenient read-out options, ease-of-use, low cost, and often sufficient diagnostic accuracy.

Microarrays are powerful tools for sensitive multi-parameter biochemical analysis. Recently, it has been demonstrated that microarrays printed onto nitrocellulose substrates can be employed for multiplexed lateral flow analysis. While multiplexed lateral flow assays could prove valuable for instance in comprehensive on-site diagnostic devices, immunochromatography as it is employed in lateral flow assays presents very different conditions for analysis when compared to well-based planar microarray assays.

The influence of kinetic parameters on adsorption/desorption and breakthrough curves in affinity chromatography has been studied extensively. The time-dependent shape of a travelling analyte zone through a column subsequent to a plug injection has been shown to vary deterministically according to the kinetic constants of the interaction between reactant and binder on the solid phase.

Flow assay methods and devices are today only aiming to measure, quantitatively or qualitatively, the presence of a certain substance, WO2003025573 ('573) and WO2007063423 ('423). Both document '573 and '423 uses multispot arrays to improve the statistics. However the depletion of reactant in upstream spots, resulting in downstream spots displaying lower levels of reactant binding in most cases, indicates that downstream spots are unsuitable as replicates of the first.

SUMMARY OF THE INVENTION

The present invention relates to a method for estimating or determining kinetic characteristics such as $k_{on}$- and $k_{off}$-rates. The method could be used in a microassay device for screening or ranking of markers or affinity binders, for example. It could further be used to qualitatively control the affinity of antibodies to antigens or allergens. Additionally, the method could be used for characterising the distribution of binding capability for a pool of antibodies or polyclonal antibodies.

According to one aspect of the present invention, the method for estimation of kinetic characteristics for the formation of a complex AB by interaction of reactants A and B, comprises the steps of:

a) providing a lateral flow substrate matrix, wherein the substrate matrix comprises at least a first spot and a second spot having immobilized reactant B, wherein the second spot is positioned in a direction downstream of the first spot;

b) causing a sample with an amount of reactant A to flow through the substrate matrix so that the sample is sequentially contacted with the first spot and the second spot;

c) measuring a first signal related to the amount of reactant A captured by the immobilized reactant B on the first spot;

d) measuring a second signal related to the amount of reactant A captured by the immobilized reactant B on the second spot;

e) estimating the ratio of the first signal to the second signal; and f) based on the ratio obtained in step e) estimating the kinetic characteristics for the formation of the complex AB.

According to another embodiment the sample comprises a population of reactants having affinity to the immobilized reactant B, and wherein the kinetic characteristics variability of the population is estimated.

According to yet another embodiment the sample comprises a population of reactants having affinity to the immobilized reactant B, and wherein the estimated kinetic characteristics comprise the dissociation rate constant ($k_{off}$) for the dissociation of the complex AB.

In another embodiment the estimated kinetic characteristics comprise the formation rate constant ($k_{on}$) for the formation of the complex AB by interaction of the reactants A and B.

According to yet another embodiment the lateral flow is a capillary or centrifugal flow, electroosmotic or electromagnetic flow or magnetophoresis flow or any other suitable flow.

According to yet another embodiment each spot is isolated from each other, while in another embodiment the spots are in the form of a continuous line.

In yet another embodiment, after step b) above the captured reactants are labelled or coloured using a detectable label.

In another embodiment the detectable label is gold or fluorescent nanobeads or marker or a radiolabled substance or any other suitable label.

In yet another embodiment the membrane is pre-soaked with a suitable buffer prior to sample addition.

Another aspect of the present invention is a method for estimating the kinetic characteristics of the dissociation of a complex AB into reactants A and B, comprising the steps of:

a) providing a lateral flow substrate matrix, wherein the substrate matrix comprises at least a first spot having a complex of AB formed thereon;

b) causing a washing buffer to flow through the substrate matrix so that the washing buffer is contacted with the first spot;

c) intermittently or continuously measuring a signal related to the amount of complex AB on the first spot providing a signal profile of complex AB as a function of time;

d) estimating kinetic characteristics for the dissociation of the complex AB based on the signal profile obtained in step c).

In another embodiment the estimated kinetic characteristics comprise the dissociation rate constant ($k_{off}$) for the dissociation of the complex AB.

According to yet another embodiment the lateral flow is a result of capillary or centrifugal flow, electro-osmotic or electromagnetic flow, magnetophoresis or any other suitable way.

In another embodiment is at least one of the reactants A and B of the complex AB coloured or labelled using a detectable label.

In another embodiment the detectable label is selected from gold or fluorescent nanobeads.

DETAILED DESCRIPTION OF THE INVENTION

In the present application the term "spot" is used not only in the sense of an isolated mark but could also include a continuous line of spots.

In the present application the terms "estimation" and "estimate" include also the terms "determination" and "determinate".

In the present application the term "binder" is referred to the reactant that is immobilized on the spots.

By letting a flow of a sample containing various reactants pass over spots immobilized with another reactant, the interaction between the reactants in the sample and the immobilized reactant can be measured. This is known to a person skilled in the art. But, the method of studying the difference between the interactions in one spot with the ones further down in the flow is new. This is also true for the estimation of kinetic characteristics related to dissociation that is based on the same principle.

The present invention relates to the formation and dissociation of complexes and the kinetic characteristics related to these phenomena. These characteristics could be for example formation or dissociation constants $k_{on}$ and $k_{off}$. When estimating the kinetic characteristics for dissociation, a washing buffer is used to flow over the spots immobilized with a complex whereas when estimating the association constants a flow of a sample containing one or more reactants is provided.

Without being bound by theory, it is believed that the time-evolution of binding of the one or more reactants A1, A2, etc is described by a system of coupled partial differential equations, one for each reactant. The equations describe the mass flow due to a) diffusion, b) convection, c) reaction. The reactions are the formation of complex AB from A (reactant)+B (capture spot) with time t, according to the dynamic equilibrium relation $$\frac{\partial AB}{\partial t} = k_{on} * A * B - k_{off} * AB.$$

In the calculation mode when practicing the present invention one does not use average values but rather the actual values of the signals from the various spots. The present invention does not involve advanced and expensive equipment unlike SPR detection (Surface Plasmon Resonance) and analogous techniques. The present invention combines the portability, ease of use and short assay time of lateral flow assays with the more accurate measurements and multiplexity of microarrays. Additionally, the present invention allows measurements at only one point in time, and furthermore, the assay of the present invention is fast which facilitates measurements including measurements of high off-rates.

EXAMPLES

Figure 1:
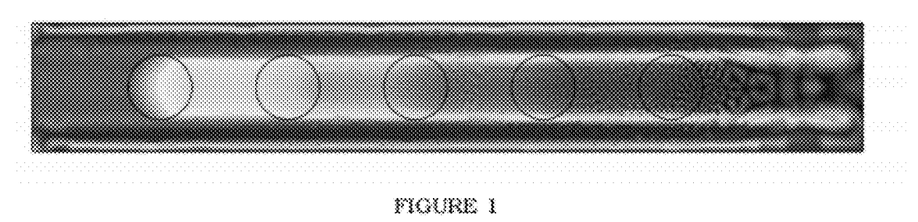
FIG. 1. Results from theoretical analysis, depletion of applied reactant.

As surface material for the microarray printing, Millipore HF090MC100 nitrocellulose strips are used. The strips are pre-fabricated with a cardboard backing and are cut into smaller segments of 1 cm width and 3 cm in length (FIG. 1). The thickness of the membrane is approximately 135 µm. A consumer-grade glue ("Skollim", Casco) is used to attach the strips to the glass slide support. For printing, a Nanoplotter 1.2 (Gesim) is used, and one drop of approximately 300 pL is deposited in each spot, producing arrays with proteins with high affinity, for example antibodies such as Affibody™ molecules, in rows with 40 downstream identical spots for each binder. After spotting the arrays, the slides are kept in room temperature during 24 hours before used for assays. Prior to performing the assay, a stretch of industrial grease (Spezialfett #3500, Heraeus) of approximately 2 mm width and 2 mm thickness is applied on one end of the strip to create a hydrophobic barrier, with room for a sample application window which could harbor at any one time no more sample than around 30-50 µl (in form of a liquid drop). Thus, the sample only travels beneath the hydrophobic barrier through the membrane and not on top of the strip. A patch of a coarse or suction membrane (Whatman) is placed at the other end of the strip, and held in place by means of a small metal weight of 100 g to provide a sink boundary for the capillary flow.

Buffers

Prior to printing, proteins with high affinity, for example antibody molecules, are diluted in phosphate buffered saline (PBS, Medicago). In all steps of the lateral flow assay, including pre-soaking of the membrane, sample dilution, dilution of gold nanobeads, and washing, a buffer consisting of PBS, 3% BSA (albumin fraction V, Merck), 1% Sucrose (Merck) and 0.5% Tween20 (VWR Scientific) is used.

Affinity Reagents

A set of proteins with high affinity, here antibody molecules, selected for affinity towards TNF-α are employed in this study. The binders are diluted in PBS to a common concentration of 100 µg/ml before printed onto the substrate. TNF-α (ProspectBio, MW=17.6 kDa) is biotinylated via coupling of NHS-linker-biotin (Pierce) to TNF-α according to the supplier's recommendations. Monoclonal anti-biotin coated gold nanobeads of 40 nm diameter (BBI) are used as detection reagents. Beads are diluted 1:3 in assay buffer from the stock concentration of OD10 (OD=optical density).

Assay Procedure

Membranes were presoaked and blocked by applying 30 µl of assay buffer in the sample application window. This volume was sufficient to presoak the whole strip within approximately 30 seconds. Subsequently, 30 µl of TNF-α diluted in assay buffer were applied to the sample application window. By the suction membrane at the other end of the strip, the sample volume could flow into the membrane. When the sample application area lost all visual sign of wetting, which was observed as a clear visible transition, 30 µl of gold nanobead suspension was added. When the application window had again dried, the next step of applying 30 µl of wash/assay buffer was started. Subsequently, the suction membrane was removed and the scanning procedure was initiated.

Image Acquisition and Data Processing

The slide is imaged by means of a table top scanner (HP Scanjet 8270, Hewlett Packard), using settings of 16 bit grayscale and 1200 dpi. Subsequently, the acquired image is inverted to account for increasing opacity corresponding to a larger amount of bound gold nanobeads and imported into Genepix 5 (Axon laboratories). From Genepix 5, median spot intensities with subtracted background are extracted. Subsequent data analysis is performed in an open source statistical environment.

Results and Statistics from Simulations

Figure 2:
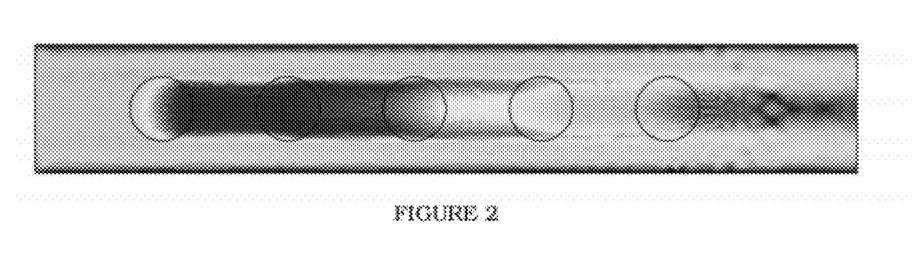
FIG. 2. Results from theoretical analysis, depletion of applied reactant.
Figure 3:
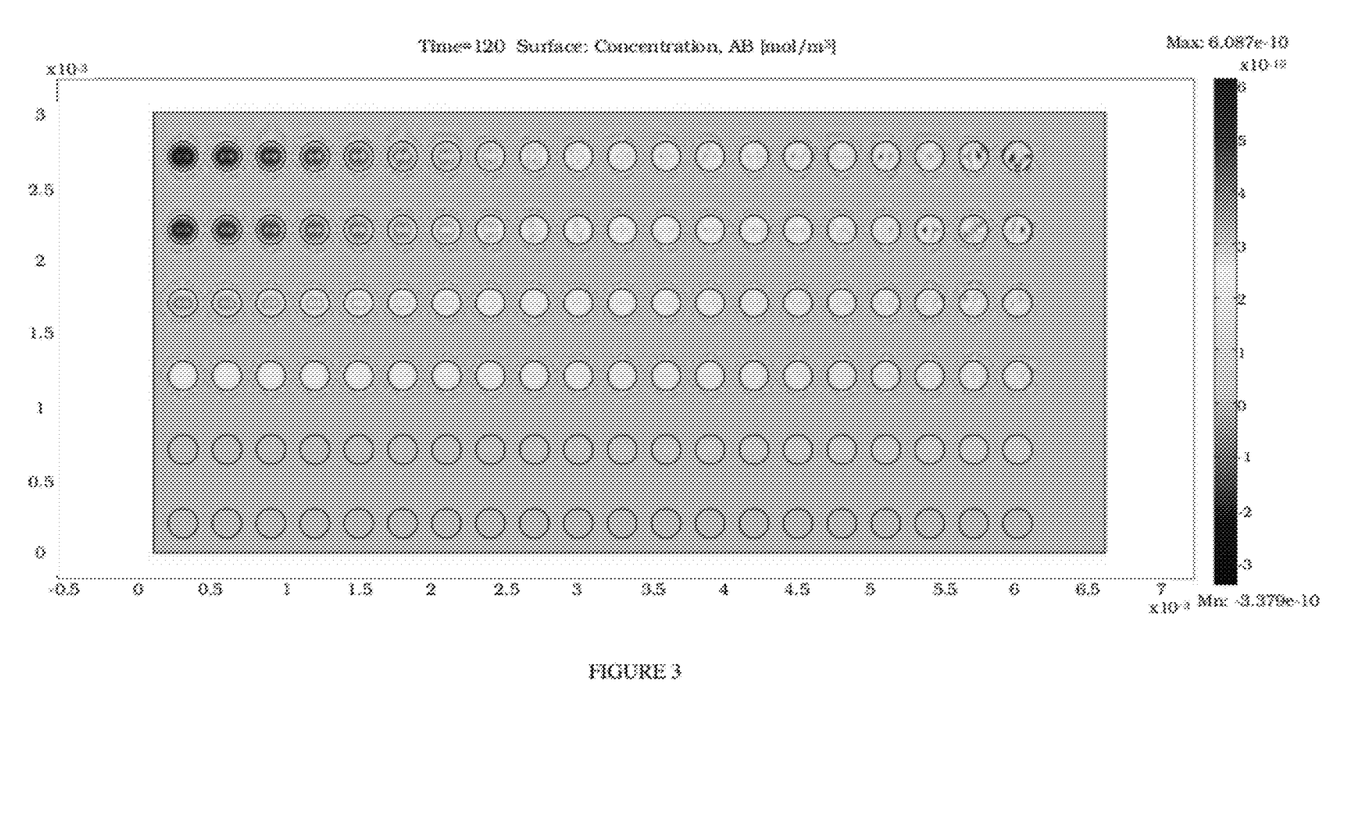
FIG. 3. Results from theoretical analysis, depletion of applied reactant.

In FIG. 1, a typical snapshot during sample application shows how the first spot effectively depletes reactant from the sample. FIG. 2 shows end stages of wash, even though there is no reactant in the washing buffer, spot 1 still supplies spot 2 with some material due to a significant off-rate.

Figure 8:
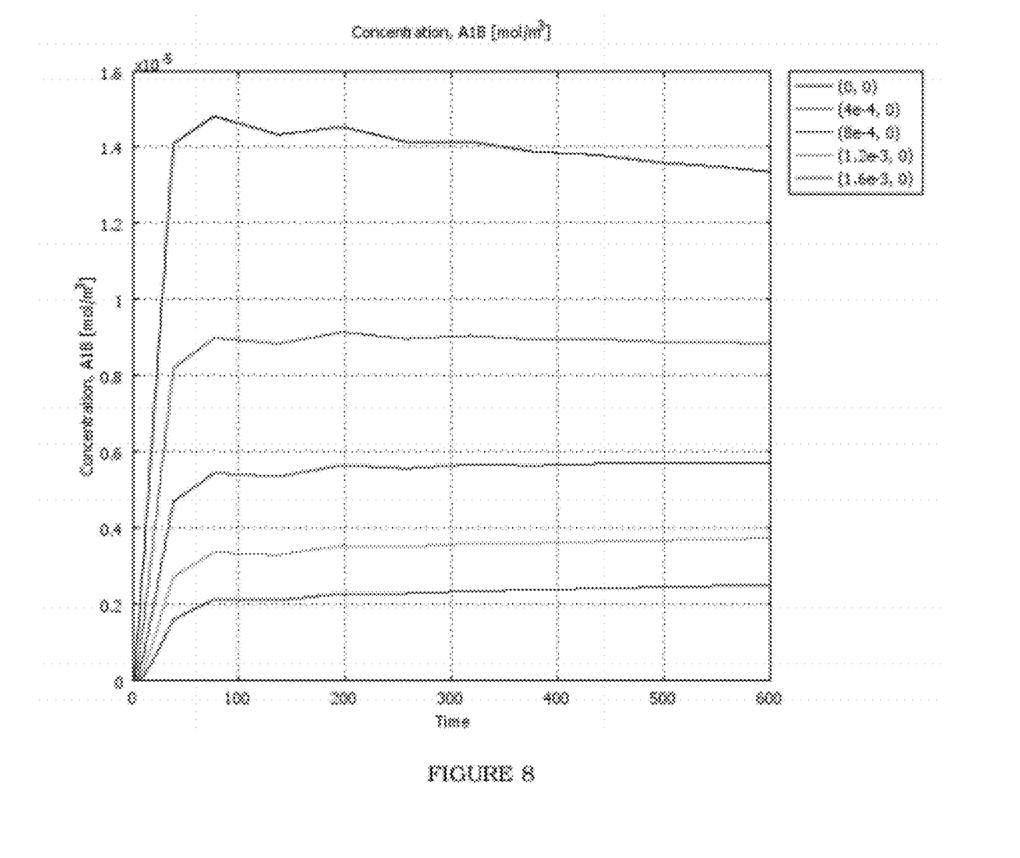
FIG. 8. Results from theoretical analysis.

Integrating the total amount of AB formed in each spot (more similar to real microarray data acquisition) and plotting the time evolution of each spot gives an insight into the mechanism of Lateral Flow assays, FIG. 8. Here it is clear that the first spot rises linearly during the sample application phase-indicating a very small off-rate, which is true—the interaction has been defined with $k_{on}$=1e6M$^{-1}$ s$^{-1}$, $k_{off}$=1e-3 s$^{-1}$, Kd=1 nM (Kd is a sorption value). Also, one can observe that the rest of the spots actually increase in intensity over time, due to the supply from spot one. In this case, a high on-rate and an even lower off-rate, 2.5e-4 s$^{-1}$, gives a very flat decay profile. If the same high on-rate, but a now high off-rate is used, the decay-curve of spot 1 is very strong, although the difference between spot 1 and spot 2 at 120 s is still large. Here, an interesting phenomenon occurs in that at 600 s, in fact the first spot shows the lowest amount of AB, and spot number 5 has the highest. The high off-rate makes the additional time that spot 1 has been in contact with wash buffer compared to spot 5 significant. If a low off-rate is used, but the on-rate is low, the first spot can not deplete the sample as efficiently, which means that the difference between spot one and spot 2 is smaller. A concurrent low on-rate, and high off-rate (here, the on-rate is 2.5e4M$^{-1}$ s$^{-1}$ and the off-rate is 1e-2 s$^{-1}$, Kd=400 nM), yields a rapidly decaying signal, with all spots at almost the same intensity.

A study of the level of spot 1, AB (600 s)/AB (100 s) results in an approximation of the time-decay behavior where it was seen that the decay constant is correlated to $k_{off}$ to a high degree, and largely unaffected by $k_{on}$. For very high on-rates, the decay appears to become slightly slower, which may be due to very efficient rebinding. Still, $k_{off}$ appears to be possible to be experimentally estimated from time-series experiments.

Figure 4:
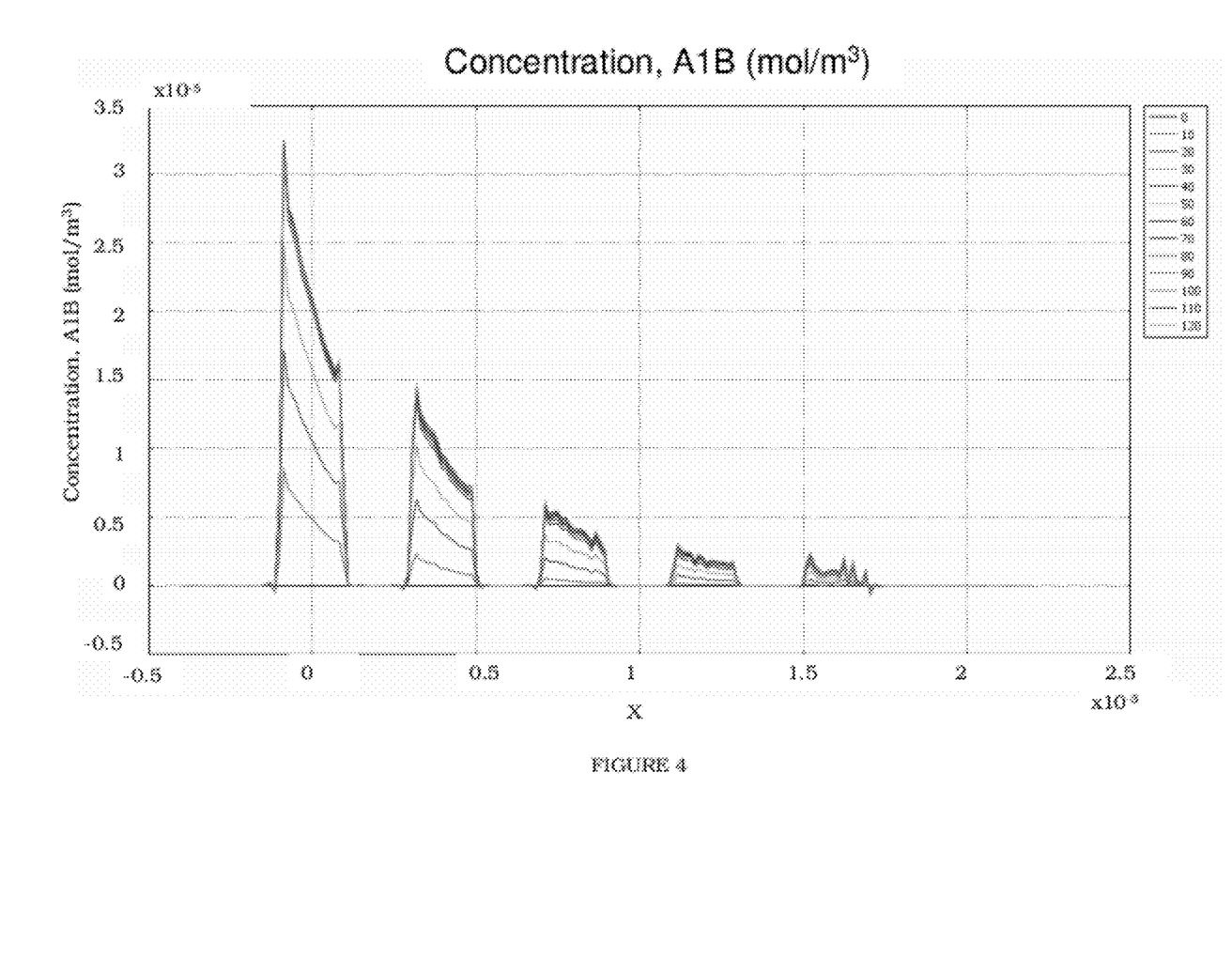
FIG. 4. Results from theoretical analysis, different time points of the assay.

FIG. 4 shows a cross section plot of the level of formed analyte-binder complex inside spots one to five at different time points during the sample application phase as indicated by the different lines. In this example, the spot complex appears to stabilize after 40 seconds.

Figure 5:
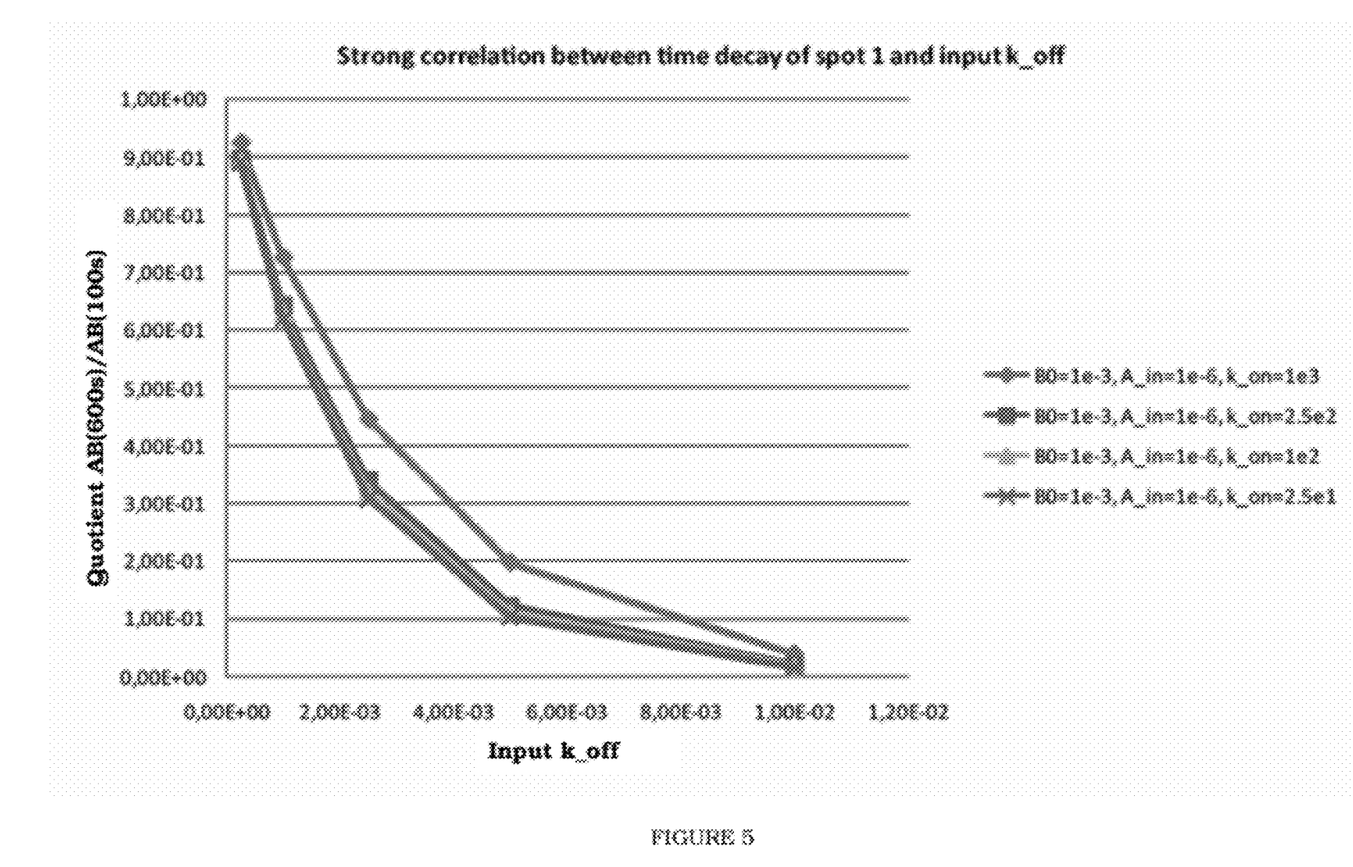
FIG. 5. Results from theoretical analysis, level of spot 1, time decay behavior.

A rough approximation of the time decay behavior can be seen by studying the level of spot 1, AB (600 s)/AB (100 s). It can be seen that the decay constant is correlated to $k_{off}$ to a high degree and largely unaffected by $k_{on}$, FIG. 5.

Figure 6:
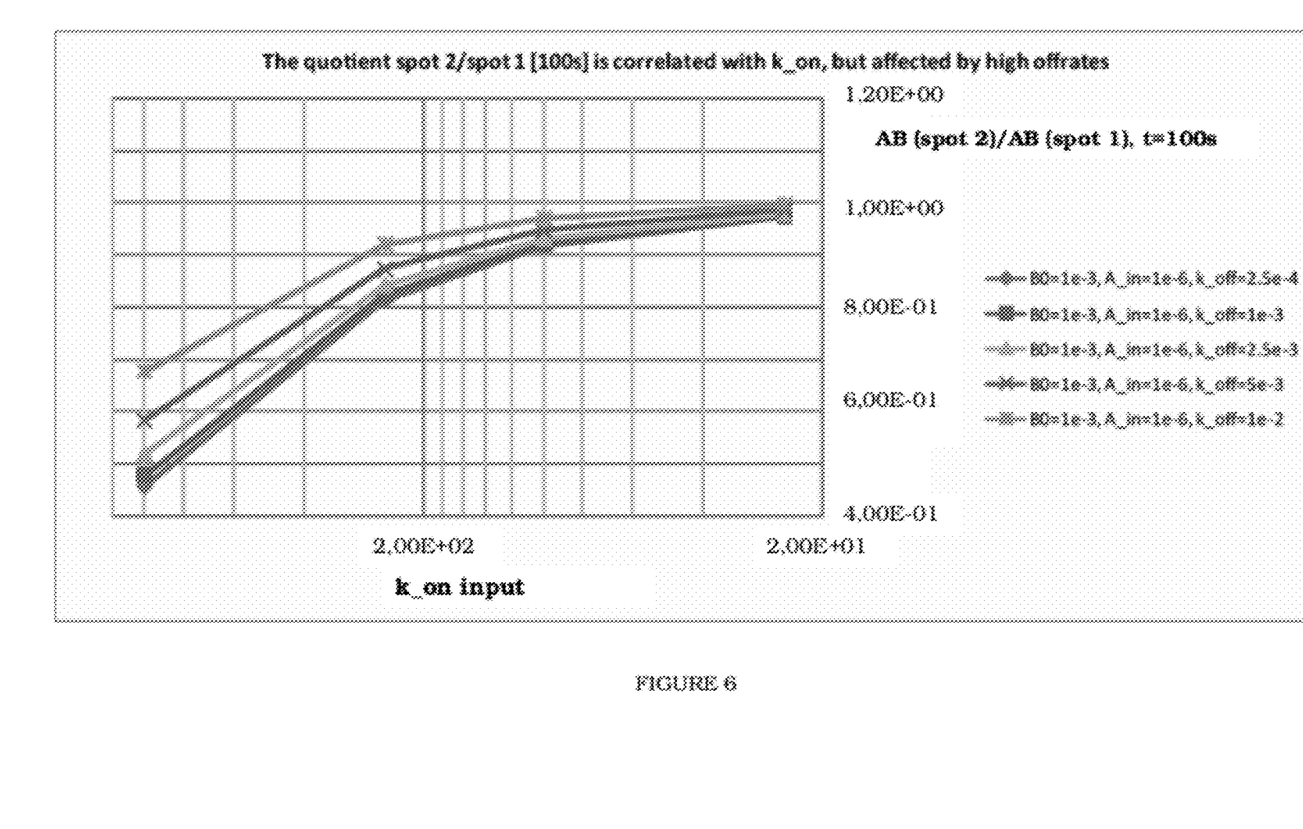
FIG. 6. Results from theoretical analysis.

In FIG. 6, it is shown that spot one can deplete the reactant from the flow, which means that spot 2 will not normally rise as high as spot 1. If the on rate is high enough, and the capacity of the spot is also sufficient, the buildup of AB on the spot is only mediated by the on-rate, which means that the quotient spot 2/spot 1 could be informative regarding the on-rate. Here, one can see that there is such an effect, at least in theory. The higher the on-rate, the lower the quotient between spot 2 and spot 1 at 100 s. However, very high off-rates diminish this "stealing" effect to a substantial degree. If the off-rate has been estimated to be <2.5e-3 s$^{-1}$, the fit is very good. If one accounts for the dependency of $k_{off}$ on the spot 2/spot 1 value, it is possible to incorporate this knowledge into a correction factor. Using the correction factor, it is possible to estimate $k_{on}$ values from the spot 2/spot 1 quotient even at high off-rates. As long as the reactant concentration remains sufficiently low, below A/B=1e-3, the $k_{on}$ value is robust. For higher values of A, the drop between spots becomes less dramatic, due to the first spot having problems depleting all incoming material. Further, if the reactant concentration is known, as in the case of a dilution series, it may be possible to reveal $k_{on}$ from the total intensity of spot 1 at 100 s (given low enough off-rates).

Figure 7:
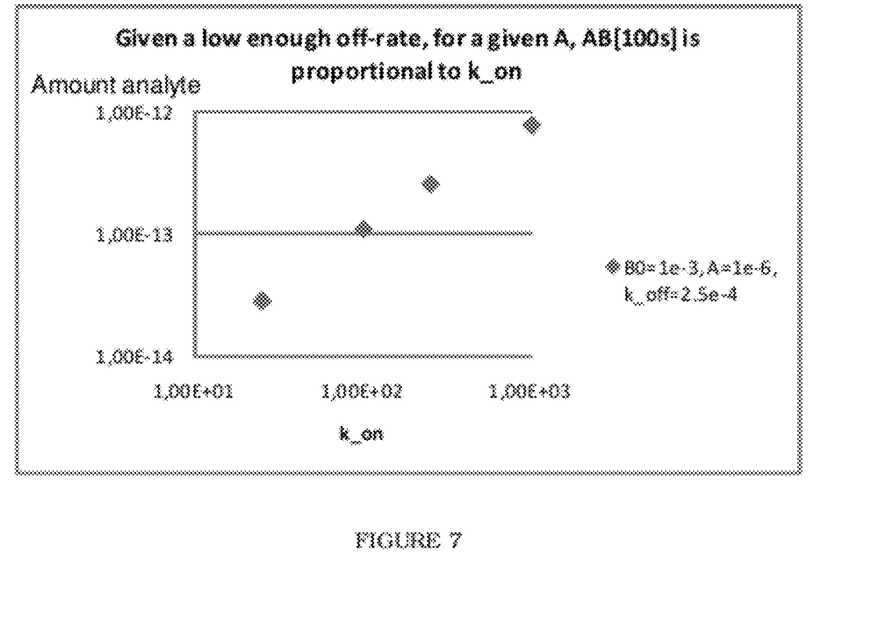
FIG. 7. Results from theoretical analysis.

If the analyte concentration is known, as in the case of a dilution series, it may be possible to reveal $k_{on}$ from the total intensity of spot 1 at 100 s (given low enough off-rates), FIG. 7.

Relevant model parameters were varied, in order to find or rule out important potential correlations that might be useful. The parameters that were varied and perturbed were A, B, $k_{on}$ and $k_{off}$. Thus far, it has been outside of the scope of the study to also vary the flow velocity, the time of applied sample, the size and position of spots, and other factors that may later be found to be important.

The parameters were varied as thus:
A=[1e-8, 1e-7, 1e-6, 1e-5, 1e-4, 1e-3, 1e-2] [mol/m3]
B=[1e-6, 1e-5, 1e-4, 1e-3] [mol/m3]
$k_{on}$=[2.5e1, 1e2, 2.5e2, 1e3] [m3/mol/s]
$k_{off}$=[2.5e-4, 1e-3, 2.5e-3, 5e-3, 1e-2] [1/s]
Non-varied parameters were:
Flow velocity=2e-4 [m/s]
D (spot size)=200e-6 [m]
distance spot-spot=200e-6 [m]
time of application of sample=60 [s]
total time of wash=600-60=540 [s] (although the result at 100 or 120 s is good to use as the experimental endpoint analogue)

The invention claimed is:

1. Method for estimation of kinetic characteristics for the formation of a complex AB by interaction of reactants A and B, comprising the steps of:
  a) providing a lateral flow substrate matrix, wherein the substrate matrix comprises at least a first spot and a second spot having immobilized reactant B, wherein the second spot is positioned in a direction downstream of the first spot;
  b) causing a fluid sample with an amount of reactant A to flow through the substrate matrix so that the sample is sequentially contacted with the first spot and the second spot and the complex AB is formed at each of the first spot and the second spot;
  c) measuring a first signal related to the amount of reactant A captured by the immobilized reactant B in the complex AB on the first spot;
  d) measuring a second signal related to the amount of reactant A captured by the immobilized reactant B in the complex AB on the second spot;
  e) estimating the ratio of the first signal to the second signal; and
  f) based on the ratio obtained in step e) estimating kinetic characteristics comprising the formation rate constant (kon) and/or the dissociation rate constant (koff) for the formation and/or dissociation, respectively, of the complex AB.

2. Method according to claim 1, wherein the sample comprises a population of reactants A having affinity to the immobilized reactant B, and wherein the kinetic characteristics of the population of reactants A are estimated.

3. Method according to claim 1, wherein the sample comprises a population of reactants A having affinity to the immobilized reactant B, and wherein the estimated kinetic characteristics comprise the dissociation rate constant (koff) for the dissociation of the complex AB.

4. Method according to claim 1, wherein the estimated kinetic characteristics comprise the formation rate constant (kon) for the formation of the complex AB by interaction of the reactants A and B.

5. Method according to claim 1, wherein the lateral flow is a capillary flow, centrifugal flow, electro-osmotic flow, electromagnetic flow, or magnetophoresis flow.

6. Method according to claim 1, wherein each spot is isolated from each other.

7. Method according to claim 1 wherein the spots are in the form of a continuous line.

8. Method according to claim 1 wherein the captured reactant is coloured or labelled using a detectable label.

9. Method according to claim 8 wherein the detectable label is selected from gold or fluorescent nanobeads.

10. Method according to claim 1 wherein the substrate matrix is pre-soaked with a suitable buffer prior to sample addition.

11. Method according to claim 1, wherein the first signal related to the amount of reactant A captured by the immobilized reactant B in the complex AB on the first spot is measured two or more times in a defined time period.

12. Method according to claim 1, wherein the second signal related to the amount of reactant A captured by the immobilized reactant B in the complex AB on the second spot is measured two or more times in a defined time period.

13. Method according to claim 1, further comprising causing a washing buffer to flow through the matrix and over the first and second spots having the AB complex therein.

* * * * *